United States Patent [19]
Dorogi et al.

[11] Patent Number: 5,778,894
[45] Date of Patent: Jul. 14, 1998

[54] METHOD FOR REDUCING HUMAN BODY CELLULITE BY TREATMENT WITH PULSED ELECTROMAGNETIC ENERGY

[75] Inventors: Peter Ladislaus Dorogi, Norwalk; John Patrick McCook, Guilford, both of Conn.

[73] Assignee: Elizabeth Arden Co., New York, N.Y.

[21] Appl. No.: 778,497

[22] Filed: Jan. 3, 1997

Related U.S. Application Data

[60] Provisional application No. 60/015,557 Apr. 18, 1996.

[51] Int. Cl.⁶ ................................ A61B 19/00
[52] U.S. Cl. .................... 128/898; 601/15; 607/71; 606/33
[58] Field of Search ................. 128/898, 736; 604/49; 606/33, 28; 607/101, 102, 156, 154, 100, 96, 108, 103, 2, 71; 601/15

[56] References Cited

U.S. PATENT DOCUMENTS

| | | | |
|---|---|---|---|
| 4,086,922 | 5/1978 | Henderson | 601/19 |
| 4,124,030 | 11/1978 | Roberts | 607/71 |
| 5,018,521 | 5/1991 | Campbel . | |
| 5,295,955 | 3/1994 | Rosen et al. | 604/22 |
| 5,443,487 | 8/1995 | Guibert et al. | 607/101 |
| 5,458,596 | 10/1995 | Lax et al. | 606/31 |
| 5,628,771 | 5/1997 | Mizukawa et al. | 607/102 |

FOREIGN PATENT DOCUMENTS 4089068  7/1990  Japan .

OTHER PUBLICATIONS

Rehab and Therapy Products Review. Jul./Aug. 1992 by Jeffrey Lipsky.

Magnatherm Product Brochure—1995.

*Primary Examiner*—Aaron J. Lewis
*Assistant Examiner*—Kelly O'Hara
*Attorney, Agent, or Firm*—Milton L. Honig

[57] ABSTRACT

A method for treating cellulite is provided involving deep heating of the cellulite afflicted areas on the body. A preferred method of deep heating is by applying electromagnetic waves in a pulsed manner.

3 Claims, No Drawings

METHOD FOR REDUCING HUMAN BODY CELLULITE BY TREATMENT WITH PULSED ELECTROMAGNETIC ENERGY

This is a continuation of U.S. Provisional application 60/01557 filed Apr. 18, 1996, now abandoned.

BACKGROUND OF THE INVENTION

1. Field of the Invention

The invention concerns a method for treating human cellulite on afflicted areas of the body to render such areas more aesthetically pleasing.

2. The Related Art

Cellulite is aesthetically displeasing. The condition is generally recognized by the dimpled appearance of skin. It is particularly apparent on thick skin, such as the thigh area. The dimpling effect is also commonly called the "mattress phenomenon" because of the periodic dimpling and bulging resembling a stuffed mattress. Mattressing becomes more apparent when the skin is pinched between the fingers. The "pinch test" may be used as a gross determination of the severity of cellulite.

Histologically, the appearance of cellulite is determined by the sex-linked distribution of female fat. Cellulite appears when subcutaneous or adipose tissue projects upwardly as rounded chambers into the overlying dermis. These molecules of fat deeply indent the dermis and approach the surface, creating the mattress phenomenon. In men, the junction between the dermis and subcutaneous tissue of flat is without deep extensions of fat into the overlying dermis.

From a cosmetic point of view, cellulite is a source of concern and distress to women. Lumpy-bumpy skin is unpleasant to feel and is often tender. This concern and distress are particularly true among overweight women, among whom more than fifty percent exhibit some degree of cellulite.

Over the years many cosmetic creams have been offered as treatments for cellulite. Claimed actives in these creams include caffeine, nicotinates and a host of vasodilators and counter-irritants such as methyl salicylate.

Electro-mechanical methods have also been suggested. For instance, Japanese Patent application 04-89068, published Jul. 8, 1992, reports on a high-frequency electromagnetic wave device with a probe that when brought in contact with a skin area improves proper tension of the skin and combats cellulite. The high frequency utilized is fixed at about 1 Mhz. While the disclosed Japanese device may be useful, there still appears to be great need for improvement in the treatment of cellulite through physical devices.

Accordingly, it is an object of the present invention to provide an improved treatment for reducing cellulite.

Still another object of the present invention is to provide a method for reducing cellulite which improves upon earlier disclosures applying high-frequency electromagnetic waves to the body.

These and other objects of the present invention will become more readily apparent from consideration of the following summary, detailed description and examples.

SUMMARY OF THE INVENTION

A method is provided for retarding and reversing cellulite on the body by deep heating the cellulite afflicted area with electromagnetic waves in a pulsed manner.

DETAILED DESCRIPTION

It has now been found that the problems of cellulite can be remedied by application of deep heating to the afflicted area. The preferred method to accomplish deep down heating is through pulsed electromagnetic wave application. More specifically, short wave diathermy is applied in an inductive therapy. This modality may employ a drum-shaped applicator containing a coil inside. The drum applicator is either spaced from the body or is put in direct contact with toweling which is on the afflicted area of the body to be treated. The applicator employs shielding to screen out electrostatic energy. This allows more electromagnetic energy into the muscle tissue without the risk of electrostatic energy causing surface burns. Many short wave diathermy equipment manufacturers offer two independent drum applicators. These are designed to be used together to treat one area from two directions, to treat two areas at the same time or to treat one area both directly and remotely at the same time.

A most preferred manner for operating the diathermy is in a pulsed electromagnetic field mode (PEMF). Most preferable pulsing operates at 27.12 Mhz. Other useful but less desirable frequencies are 2.45, 13.56 and 40.68 Mhz. They are pulsed usually between 70 and several hundred times per second, depending on the setting of the instrument. They have a pulse width between 20 microseconds and 400 microseconds, with an intensity of up to 1,000 watts per pulse. Ordinarily the power per pulse will range between 1 and 120, preferably between 10 and 60, optimally about 40 watts.

The short burst (pulse) of PEMF's creates an intense wattage, which oscillates off and on during a procedure, many times per second. This allows the blood stream to carry off the heat generated in the tissue before there is a noticeable buildup of heat, by the short blasts, of what is essentially short wave diathermy. Therapeutic heat is delivered deep down into the musculature of the body. For purposes of the present method, a Magnatherm brand device (Magnatherm Model 100 SS) can be employed, and is available from International Medical Electronics Ltd. of Kansas City, Mo.

The method may be further enhanced by physically massaging the cellulite afflicted area prior to deep heating. Physical massaging the body in a vigorous manner breaks down connective tissue. Sufficient force is required. The force may be applied directly by hand or through some other instrument such as a paddle applied to the afflicted areas. Thereafter the connective tissue is regenerated and redistributed in a more even manner through application of deep heating electromagnetic waves which stimulate blood flow, oxygenate of the tissue, and thereby speed tissue regeneration. The method may include alternating between massage and deep heating steps.

EXAMPLE

A clinical study was conducted to determine whether pulsed deep down heating through diathermy treatment improves the appearance of cellulite on legs compared to pre-treatment observations.

The study covered a four month period with two groups of panelists. Group 1 began the study approximately one month earlier than Group 2. Four subjects from Group 1 (marked below with an asterisk) continued on with the same treatment regimen of Group 2 for an additional three months for a total of four months of treatment. Diathermy treatment rates, powers, and times administered during each stage, and the subjects completing each stage are summarized below.

| Rate | Power | Time (min.) |
|---|---|---|
| | Group 1 | |
| 3 | 6 | 10 |
| 12 | 12 | 20 |
| 1 | 10 | 10 |
| | Subjects | |
| | 001 | |
| | 002 | |
| | 004 | |
| | 005 | |
| | 006 | |
| | 008 | |
| | 009 | |
| | 010 | |
| | Group 2 | |
| 12 | 12 | 40 |
| 1 | 12 | 10 |
| | Subjects | |
| | 004* | |
| | 005* | |
| | 006* | |
| | 010* | |
| | 012 | |
| | 013 | |
| | 014 | |
| | 015 | |
| | 016 | |
| | 017 | |
| | 018 | |

Subjects were positioned horizontally with their knees bent for diathermy treatment which was applied to the leg self-perceived to have the worst cellulite. The paddles of the diathermy machine were placed on the upper thigh for the required length of time. One paddle was positioned on the outer thigh, and the other on the inner thigh over the femoral artery.

At the baseline visit and on Wednesday of each week, cellulite on the subjects' legs, treated (T) and untreated (U), was evaluated for lumps/bumps (LB), ridges (RI), and dimples (DI). A global assessment (GL) was also recorded. A forced comparison (FC) of the front (F), side (S), and back (B) of the legs and of the legs in motion (M) was also performed by the grader. In addition, a firmness (FM) score was determined for the front, side, and back of each leg.

Significant improvements in cellulite compared to baseline are represented in the following charts by asterisks(*) at the time points and variables where significant improvements were observed. For the forced comparisons, the asterisk indicates significant difference between the treated and untreated leg. Note that there are two visit 5's. The first is the final visit for the eight subjects in Group 1 who finished the first month of the study. The second visit 5 listed is the baseline visit for the four subjects that continued on to participate in testing with Group 2. Visit 5 represents the beginning of the increased dosage for these four subjects. All attributes for Group 1 improved significantly by visit 5 except lumps/bumps on the untreated legs. For Group 2, the results only include the seven subjects who participated in all thirteen visits but not the four subjects from Group 1.

| | GL | | LB | | DI | | RI | | FC | | | | | | FM | | | | |
|---|---|---|---|---|---|---|---|---|---|---|---|---|---|---|---|---|---|---|---|
| | | | | | | | | | F | | B | | M | | F | | B | | S | |
| | T | U | T | U | T | U | T | U | T | U | T | U | T | U | T | U | T | U | T | U |
| GROUP 1: SIGNIFICANT IMPROVEMENT | | | | | | | | | | | | | | | | | | | | |
| V2 | | | | | | | | | | | | | | * | | | | | | |
| V3 | | | | | | | | | | | | | | | | | | | | |
| V4 | * | | | | | | | | * | | * | | | | | | * | * | | |
| V5 | * | * | * | | | | * | * | * | * | | | | | * | | * | | | |
| V5 | | | | | | | | | | | | | | | | | | | | |
| V6 | | | | | | | | | | | | | | | | | | | | |
| V7 | | | | | | | | | | | | | | | | | | | | |
| V8 | | | | | | | | | | | | | | | | | | | | |
| V9 | | | | | | | | | | | | | | | | | | | | |
| V10 | | | | | * | | | | * | | | | | | | | | | | |
| V11 | | | | | * | | | | * | | | | | | | | | | | |
| V12 | | | | | * | | | | * | | | | | | | | | | | |
| V13 | | | | | * | | | | * | | | | | | | | | | | |
| V14 | * | | * | | * | | | | * | | | | | | | | | | | |
| V15 | * | | * | | * | | | | * | | | | | | * | | | | | |
| V16 | * | | * | | * | | | | * | | | | | | * | | | | | |
| V17 | * | | * | | * | | | | * | | | | | | * | | | | | |
| GROUP 2: SIGNIFICANT IMPROVEMENT | | | | | | | | | | | | | | | | | | | | |
| V2 | | | | | | | | | | | | | | | | | | | | |
| V3 | * | | | | * | | | | * | * | | | | | | | * | * | | |
| V4 | * | * | | | * | * | | | * | * | | | | | | | * | * | | |
| V5 | * | * | | | * | * | * | * | * | * | | | | | | | * | * | * | |
| V6 | * | * | * | | * | * | * | * | * | | | | | | | | * | * | * | * |
| V7 | * | * | * | * | * | * | * | * | * | | | | * | | | | * | * | | |
| V8 | * | * | * | * | * | * | * | * | * | | | | * | | | | * | * | | |
| V9 | * | * | * | * | * | * | * | * | * | | | | | | | | * | * | | |
| V10 | * | * | * | * | * | * | * | * | * | | | | | | | | * | * | | |
| V11 | * | * | * | * | * | * | * | * | * | | | | | | | | * | * | | |
| V12 | * | * | * | * | * | * | * | * | * | | | | | | | | * | * | | |
| V13 | * | * | * | * | * | * | * | * | * | | | | | | | | * | * | | |

Subjects in both groups also assessed the differences of cellulite on their own legs at each visit and were asked about their cellulite concerns. From this, no significant differences were observed for Group 1, the subgroup of 4 or Group 2.

Under the conditions of this test, diathermy treatment improved the overall appearance of cellulite with the greatest improvement occurring within one month. Moderate cellulite improved to a greater degree in absolute change than mild cellulite.

It is understood that the foregoing detailed description and Example is given merely by way of illustration and that many variations may be made therein without departing from the spirit and purview of this invention.

What is claimed is:

1. A method for improving the overall appearance of human cellulite on afflicted skin surface areas of the body, comprising deep heating the afflicted areas with electromagnetic waves applied by an applicator externally located over the afflicted areas, the electromagnetic waves being applied in a pulsed manner of pulse width between 20 and 400 micro seconds within a frequency range from 2.45 to 40.68 MhZ.

2. The method according to claim 1 wherein energy applied by the pulses ranges from 1 to 120 watts per pulse.

3. The method according to claim 1 wherein the frequency is between 13.56 and 40.68 MhZ.

* * * * *